US009068281B2

United States Patent
Wu et al.

(10) Patent No.: US 9,068,281 B2
(45) Date of Patent: Jun. 30, 2015

(54) MICROFLUIDIC CHIP FOR HIGH-THROUGHPUT PERFUSION-BASED THREE-DIMENSIONAL CELL CULTURE

(75) Inventors: Min-Hsien Wu, Kaohsiung (TW); Shih-Siou Wang, Kaohsiung (TW); Wan-Chen Tsai, Taichung (TW); Yu-Han Chang, Taoyuan (TW); Chia-Hsun Hsieh, Taoyuan (TW); Yen-Ting Liu, Kaohsiung (TW); Zhanfeng Cui, Taoyuan (TW)

(73) Assignee: Chang Gung University, Taoyuan (TW)

( * ) Notice: Subject to any disclaimer, the term of this patent is extended or adjusted under 35 U.S.C. 154(b) by 651 days.

(21) Appl. No.: 13/241,123

(22) Filed: Sep. 22, 2011

(65) Prior Publication Data

US 2012/0231976 A1    Sep. 13, 2012

(30) Foreign Application Priority Data

Mar. 8, 2011  (TW) .............................. 100107743 A

(51) Int. Cl.
*C40B 60/12*   (2006.01)
*C12M 3/06*    (2006.01)
*C12M 1/34*    (2006.01)

(52) U.S. Cl.
CPC ............... *C40B 60/12* (2013.01); *C12M 23/16* (2013.01); *C12M 41/00* (2013.01); *C12M 41/12* (2013.01); *C12M 41/40* (2013.01)

(58) Field of Classification Search
CPC ...... C12M 23/16; C12M 41/00; C12M 41/40; C12M 41/12; C40B 60/12
See application file for complete search history.

(56) References Cited

U.S. PATENT DOCUMENTS

| 5,916,526 A * | 6/1999 | Robbins ........................ 422/552 |
| 2005/0260745 A1* | 11/2005 | Domansky et al. ........ 435/294.1 |
| 2007/0243523 A1* | 10/2007 | Ionescu-Zanetti et al. ....... 435/4 |
| 2010/0273262 A1 | 10/2010 | Wu |

* cited by examiner

*Primary Examiner* — Nathan Bowers
*Assistant Examiner* — Gautam Prakash

(57) ABSTRACT

A microfluidic chip for three-dimensional cell culture with high-throughput perfusion includes an array of cell culture units, each unit including a cell culture medium inlet hole connecting to one cell culture medium tank, at least one micro-bioreactor, at least one microchannel and at least one medium collection and analysis tank. Each medium collection and analysis tank is connected to an air chamber with an air channel and the air chamber has negative pressure source holes to generate negative pressure to drive the culture medium. The microfluidic chip also includes an intermediate plate connected to the bottom surface of the roof, and two bottom plates detachably assembled at the bottom of the intermediate plate. The first and second bottom surfaces have micro-bioreactors and cylindrical recessed slots and the intermediate plate has corresponding holes to achieve the goal of three-dimensional cell culture using minimum experimental resources with high-throughput perfusion.

7 Claims, 19 Drawing Sheets

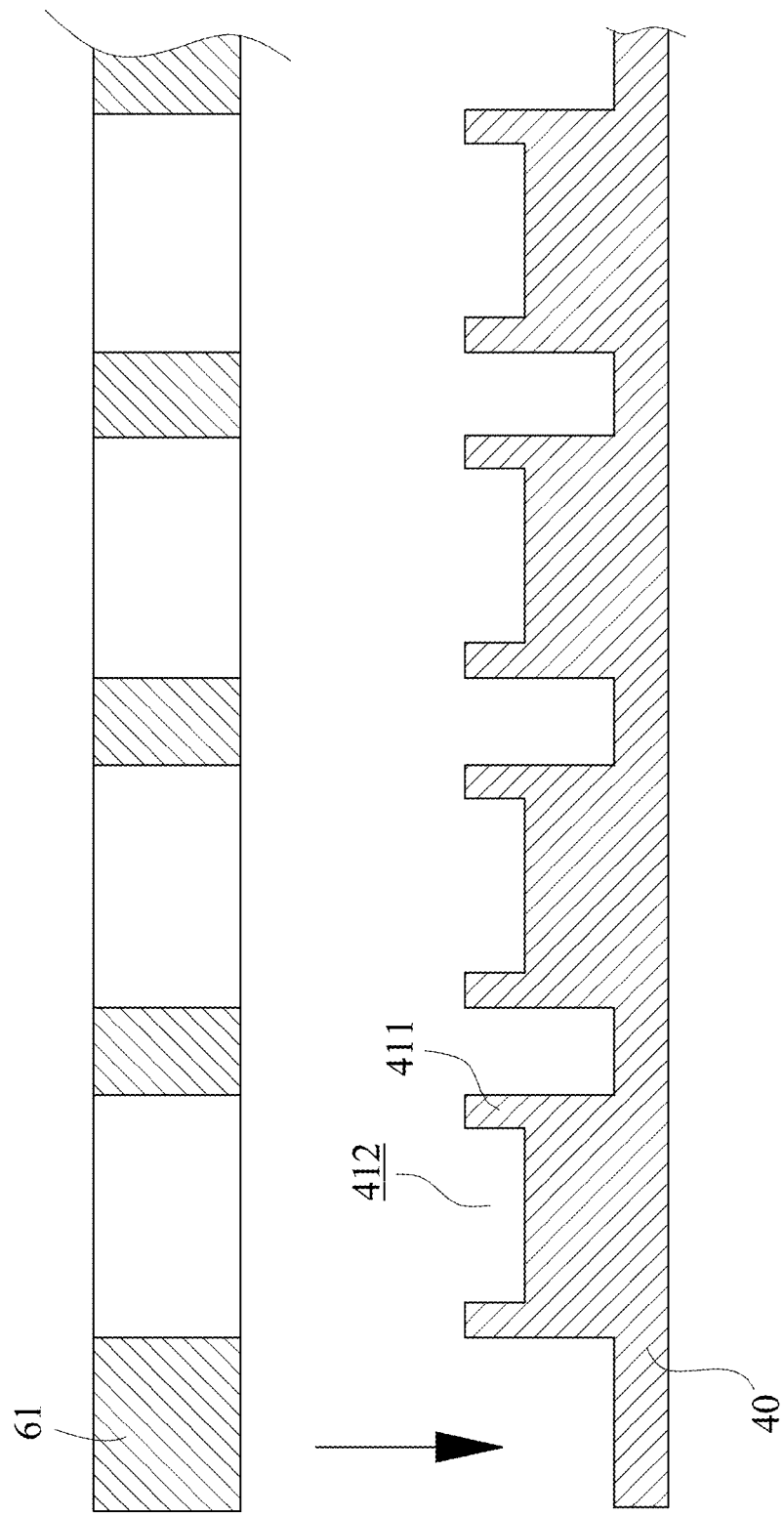

MICROFLUIDIC CHIP FOR HIGH-THROUGHPUT PERFUSION-BASED THREE-DIMENSIONAL CELL CULTURE

FIELD OF THE INVENTION

The invention is to provide a cell culture chip, especially to provide a microfluidic chip capable of carrying out high-throughput miniaturized perfusion-based three-dimensional cell culture with few experimental resources, and the device is simple, less expensive and easy to operate.

BACKGROUND OF THE INVENTION

Cell culture is a fundamental technique in life science or medical-related research. Traditional cell culture uses a simple container (such as Petri dish or multi-well microplate) as a vessel for cell culture, and this cell culture model mostly utilizes static culture and two-dimensional cell attachment culture. This type of cell culture has the following disadvantages:

(1) Due to manual replacement of the culture medium, a static cell culture may suffer the risk of microbial contamination. More importantly, such periodic medium replacement process could cause a relatively fluctuating environment, and under such improperly controlled conditions, the cellular response to the investigated conditions may become more complex.

(2) Cells cultured in the two-dimensional model, in which cells are cultured as a monolayer on a substrate surface, may have different cell physiology comparing with real (in vivo) physiological state, and under such culture conditions, the experimental results may lose authenticity.

Therefore, in order to provide a cell culture model which is stable, quantifiable and with physiological significance, the perfusion-type three-dimensional cell culture (e.g. cells are seeded within a polymeric scaffold, or in the form of multicellular spheroids) has been used in recent years. However, this kind of cell culture unit usually has complicated structure, high cost and large volume, which may not only limit the research throughput, but also consume relatively more experimental resources. More importantly, the cell culture conditions under conventional three-dimensional cell culture practices might not be regarded as homogenous mainly due to the chemical gradients that exist in these relatively large-scale three-dimensional cell culture constructs. Poorly-defined culture conditions caused by the chemical gradient phenomenon in a culture system may restrict the precise quantification of the link between cellular responses and investigated conditions. To tackle this technical hurdle, the miniaturization of perfusion-based three-dimensional cell culture is proposed.

SUMMARY OF THE INVENTION

The present invention provides a microfluidic cell culture chip capable of carrying out high throughput miniaturized perfusion-based three-dimensional cell culture, which has the following features:

(1) Simply using a negative pressure source to continuously drive fluid in multiple channels to achieve the goal of high-throughput perfusion cell culture;

(2) Incorporating with previous U.S. patent application (application Ser. No. 12/653,335) filed by the inventor to simply, efficiently and accurately prepare for a large number of small-scale three-dimensional cell-embedded gels or other biocompatible materials for high throughput miniaturized three-dimensional cell culture; and (3) This invention particularly designs a waste medium collector array module to meet the commercial standards of plastic multi-well microplate for collecting cell culture medium to further use the Microplate Reader or other compatible analysis equipment to conduct high-throughput biochemical analysis.

Therefore, different from other microfluidic cell culture chip with similar functions, the present invention can use a small amount of experimental resources to conduct high-throughput perfusion-type three-dimensional cell culture, and the device in the present invention is simple, less expensive and easy to operate. Furthermore, the present invention can provide a cell culture model which is stable, uniform, quantifiable and with physiological significance. This invention is ideal for replacing traditional cell culture operations, and the potential market is for life science or medical-related research laboratories, clinical analysis laboratories and pharmaceutical companies conducting high throughput drug screening or testing.

BRIEF DESCRIPTION OF THE DRAWINGS

FIGS. 4A-D illustrate a flow chart of filling and quantitative control of the cell culture samples on the first bottom plate.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
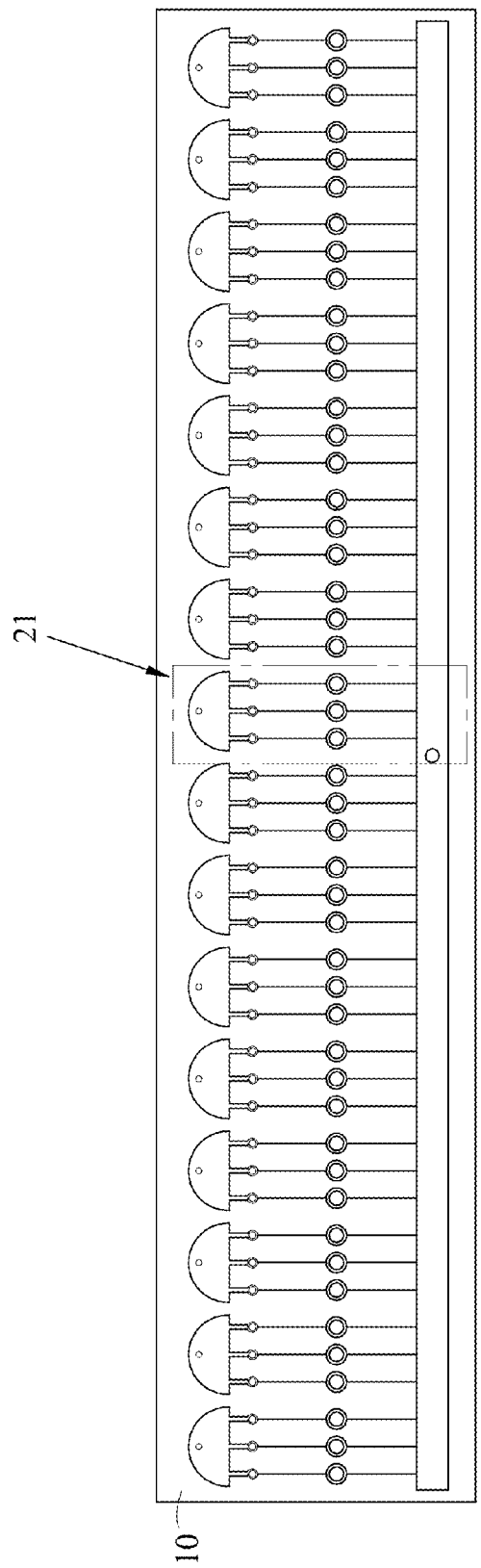
FIG. 1 illustrates a top view of the microfluidic cell culture chip in the present invention.
Figure 1A:
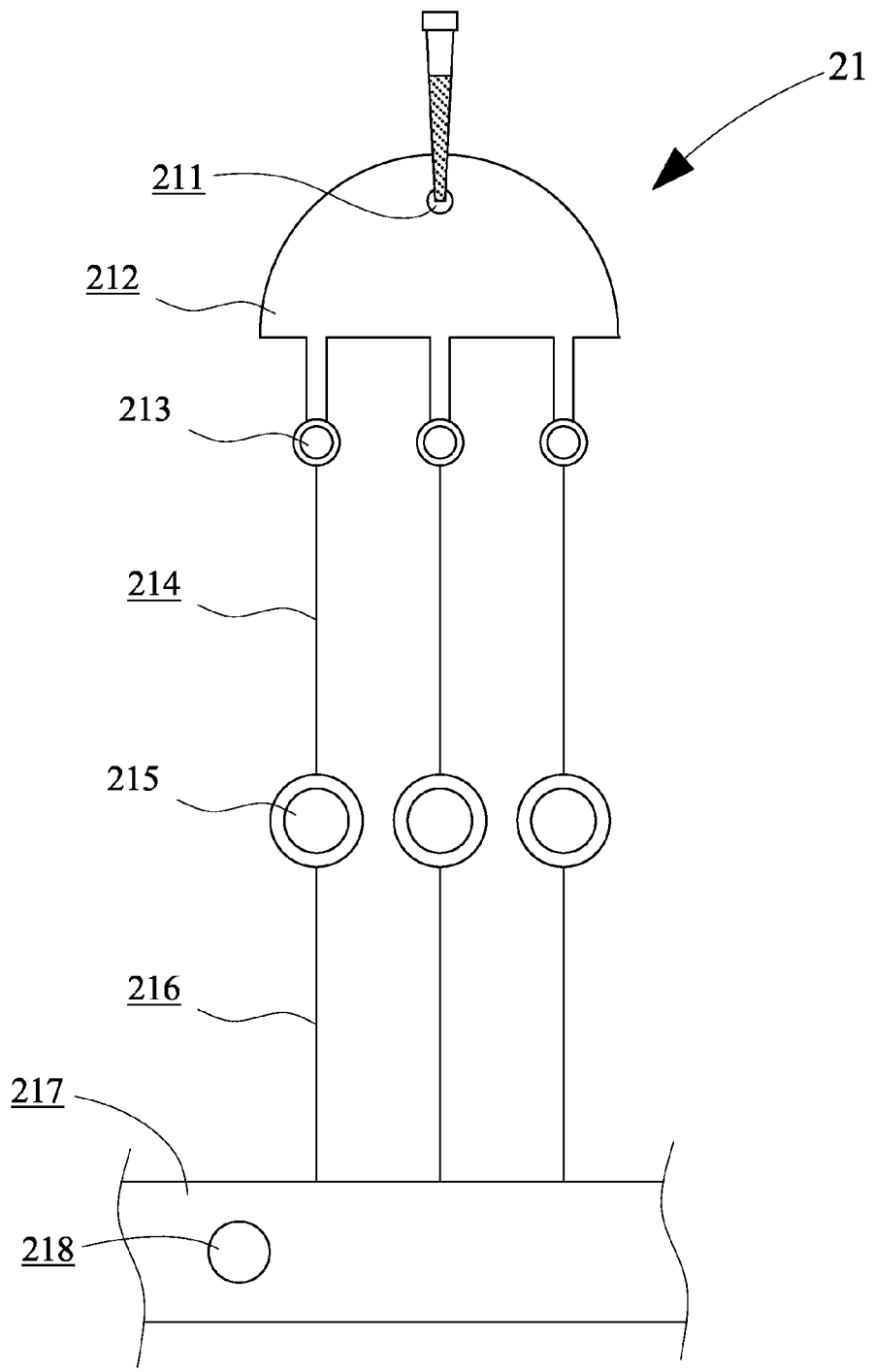
FIG. 1A illustrates a two-dimensional view of the cell culture unit in the present invention.
Figure 2:
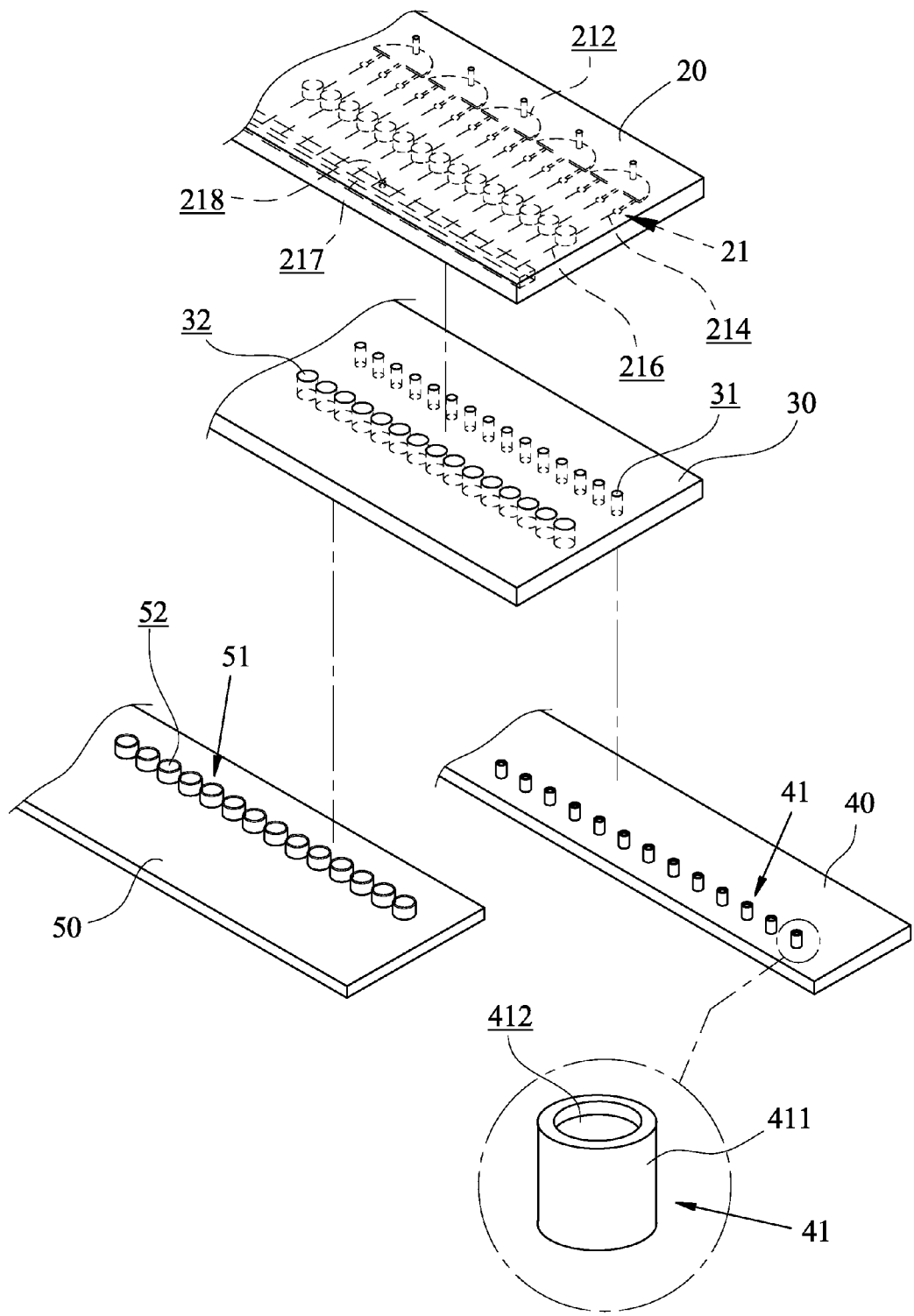
FIG. 2 illustrates one embodiment of driving the medium of the microfluidic cell culture chip in the present invention.

Referring to FIGS. 1 to 2, the present invention provides a microfluidic chip capable of carrying out high throughput miniaturized perfusion-based three-dimensional cell culture, the microfluidic cell culture chip (10) includes:

a roof (20), which has a bottom surface with a plurality of cell culture units (21), and each cell culture unit (21) includes a liquid culture medium connected to a top surface of the roof (20) through an inlet hole (211). The bottom surface of the roof (20) has a culture medium tank (212) connected with the inlet hole (211), and the culture medium tank (212) connects to a front end of three micro-bioreactors (213), wherein three rear ends of the micro-bioreactors (213) include three microchannels (214) to connect to front ends of three waste medium collector tank (215). All rear ends of the waste medium tank (215) located at the bottom surface of the roof (20) are connected to an air chamber (217) through an air channel (216), and the air chamber (217) has at least one negative pressure source hole (218) to generate negative pressure and drive the medium flow. Here, the number of the front ends of the micro-bioreactors (213) provides only one possible embodiment. The number of the microchannel (214) connected to the front end of the micro-bioreactor (213), and the number of the front ends of the waste medium tank (215) connected to the microchannel (214) are merely associated with the front end of the micro-bioreactor (213), not used for limit the present invention;

an intermediate plate (30), a top surface thereof bonded to the bottom surface of the roof (20);

a bottom plate (40) and a waste medium collector array module (50), which can both be disassembled and formed at the bottom surface of the intermediate plate (30). A top surface of the bottom plate (40) has a plurality of micro-bioreactors (41) with cylindrical chambers (412) of a cylinder (411), and a surface of the waste medium collector array module (50) has an array of waste medium collector tank (52) with cylindrical recessed slots (51) that can be directly analyzed by a commercial multi-well microplate reader (70). The intermediate plate (30), corresponding to the cylindrical micro-bioreactor (41), has the same number of connecting holes (31) to engage the micro-bioreactor (41) with cylindrical chambers (412) of the cylinder (411). Also, the intermediate plate (30), corresponding to the cylindrical recessed slots (51), has the same number of array holes (32) to engage the cylindrical recessed slots (51).

The method for bonding the intermediate plate (30) and the roof (20) in the abovementioned microfluidic chip for high throughput miniaturized perfusion-based three-dimensional cell culture may be different for different materials. For example, the intermediate plate (30) and the roof (20) are made by soft polymer (e.g. poly-dimethylsiloxand, PDMS), and the bonding method is plasma oxidation accordingly.

Referring to FIGS. 1 to 3D for detail embodiments (the embodiments are merely examples of the present invention, not limitation thereof), the present invention provides a microfluidic chip with a miniaturized three-dimensional cell culture of high-throughput perfusion, wherein the cell culture microfluidic chip (10) has sixteen cell culture units (21) and each cell culture unit (21) has three front ends (213) to engage the micro-bioreactor (41). The purpose of the design is to allow replication of each experimental condition in triplicate. If the present invention can design sixteen cell culture units (21), it can meet the high-throughput requirement to test sixteen different cell culture conditions simultaneously. As to each cell culture unit (21), it has one inlet hole (211). In terms of operation, an experimental pipet (60) is used to quantitatively load some special cell culture medium (such as the culture medium containing a drug with specific concentration) and the pipet (60) directly plugs into the culture medium holes (211) to provide the culture medium. In terms of design, the bottom of the cell culture unit (21) is connected to one air chamber (217), the top of which is connected with at least one negative pressure source hole (218), which is used to apply negative pressure to the air chamber (217) to simultaneously drive the culture medium in sixteen cell culture units (21). Operatively, when the air chamber (217) is subject to negative pressure, the cell culture medium in each cell culture unit (21) can flow through microchannel (214) to the micro-bioreactor (41), and finally connect to the front end of waste medium collector tank (52). This design is configured to achieve the goal of high-throughput perfusion cell culture.

As can be seen in FIG. 2, the present invention provides a microfluidic chip for high throughput miniaturized perfusion-based three-dimensional cell culture. In terms of structure, the microfluidic cell culture chip (10) contains three structural layers in total. In terms of design, the roof has 16 culture medium tanks (212), 48 microchannels (214), 48 air channels (216) and an air chamber (217) in the rear end. The intermediate layer contains connecting holes (31) and array holes (32) configured to engage with the cylindrical structure in the bottom plate. The bottom plate includes the micro-bioreactor chamber (41) having 48 cylindrical chambers (412) of the cylinder (411) and a bottom piece of waste medium collector array module (50) containing 48 waste medium collector tanks (52) and 48 cylindrical recessed slots (51). In terms of design, each cylindrical chamber (412) of the micro-bioreactor (41) is a cylinder (411) in appearance, and a top surface of the cylinder (411) has a cylindrical chamber (412), which is designed not only to accommodate a three-dimensional cell culture sample but also to quantitatively define the volume of such sample loading. In the design of the waste medium collector tank (52) of the cylindrical recessed slot (51), the size of the cylindrical recessed slots (51) can be designed by commercialized multi-well microplate with specifications, such as 384-well microplate. The purpose is to be compatible with commercially high-throughput biochemical analysis equipment—microplate reader (70) or combination with other biochemical analytical instruments to facilitate the follow-up analysis after cell culture. In operation, after cell culture, the waste medium collector array module (50) can be unloaded, and appropriate analytical reagent can be added to directly analyze the results by using the microplate reader (70) or compatible biochemical analysis equipment.

The microfluidic chip for high throughput miniaturized perfusion-based three-dimensional cell culture in the present invention can use polymer materials, then employ casting, injection molding, compression molding, ablation, CNC micromachining, or other microfabrication processes to fabricate the roof (20), intermediate plate (30), bottom plate (40) and waste medium collector array module (50). According to the materials used in the roof (20) and the intermediate plate (30), appropriate materials can be selected for general (bonding) technology to bond the roof (20) and the intermediate plate (30). The bottom (40) and the waste medium collector array module (50) are designed to be detachable, and when the cylindrical chamber (412) fills the three-dimensional cell culture samples with a fixed amount, the protruding cylinders (411) located at the bottom plate (40) are inserted into corresponding connecting holes (31) on the intermediate plate (30) to achieve tight engagement. Similarly, the cylindrical recessed slots (51) of the waste medium collector array module (50) are also inserted into the array holes (32) of the intermediation plate (30) in the same manner. When the roof (20), intermediate plate (30), bottom plate (40) and waste medium collector array module (50) are tightly engaged, a "microfluidic chip for high throughput miniaturized perfusion-based three-dimensional cell culture" is formed, the most important feature of which is to utilize a simple way to simultaneously and continuously drive liquid in multi-channels to achieve the goal of cell culture with high-throughput perfusion.

Figure 3A:
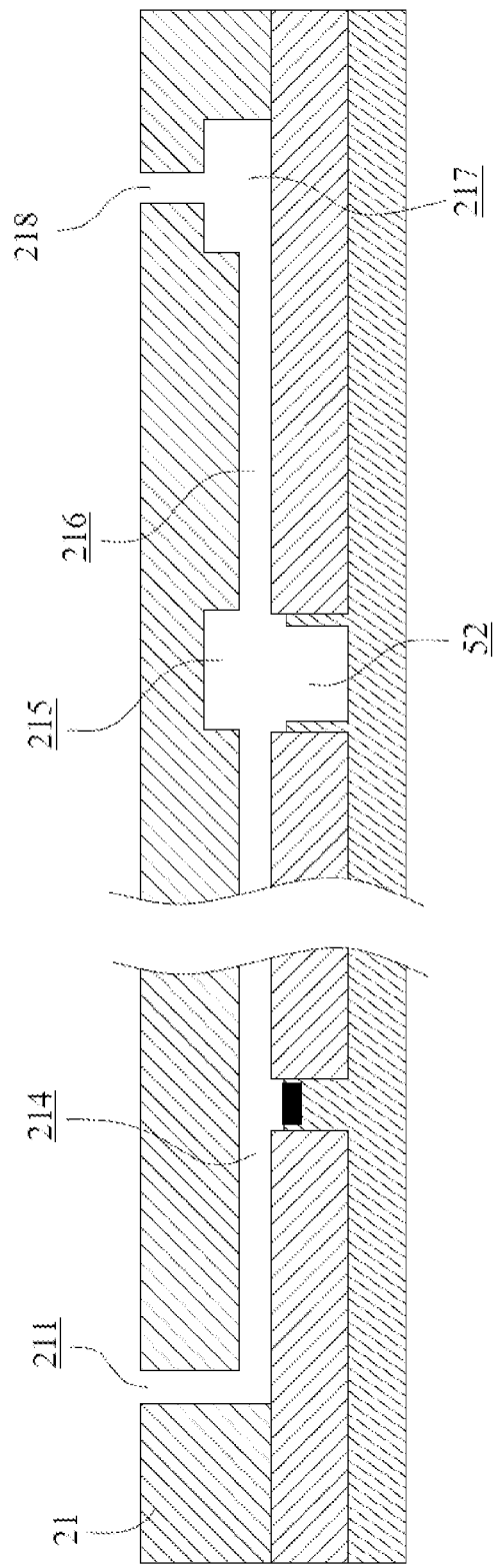
FIGS. 3A-D illustrate a flow chart of driving the medium of the microfluidic cell culture chip in the present invention.
Figure 3B:
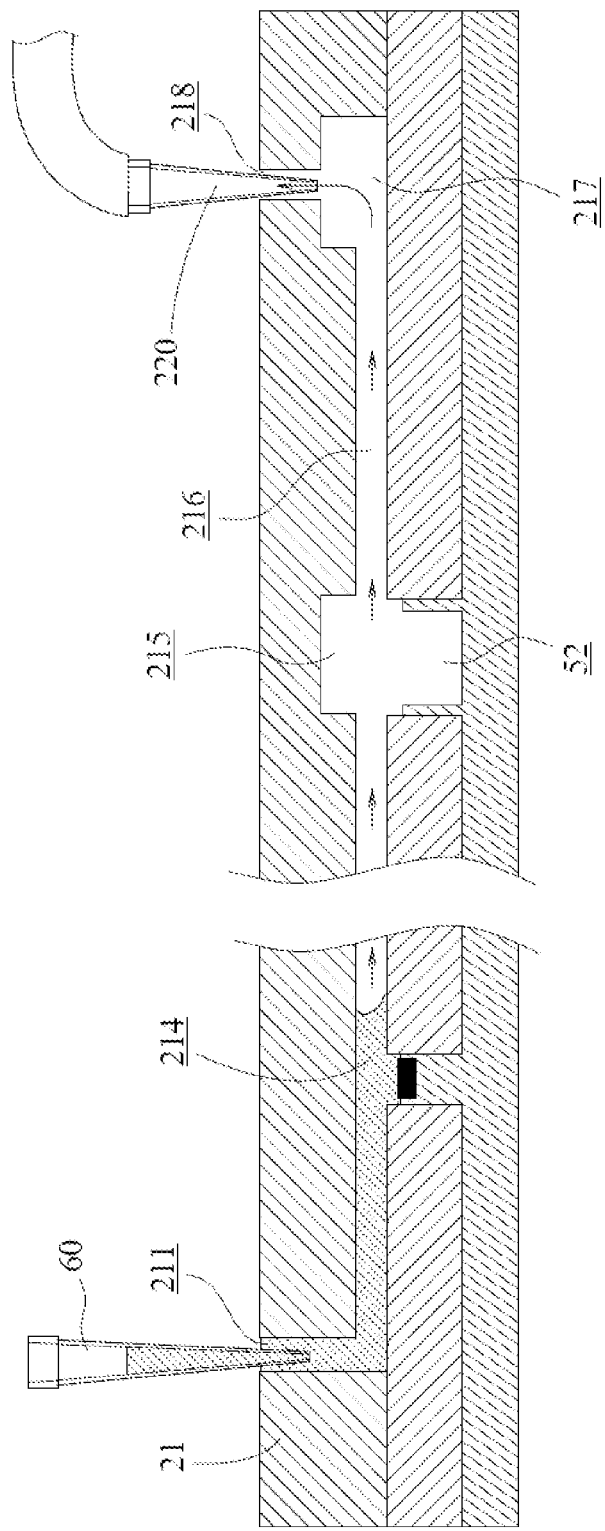
Figure 3C:
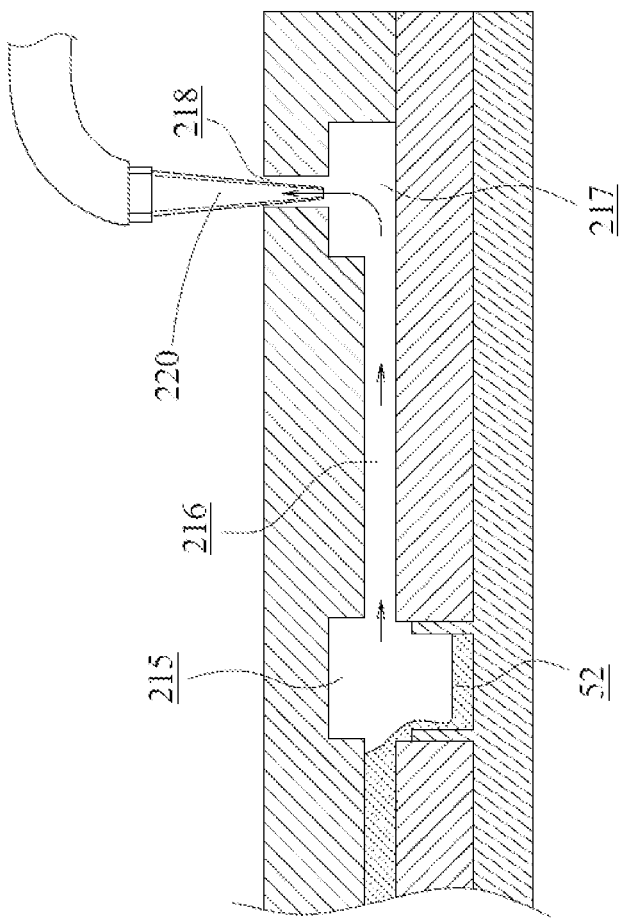
Figure 3C:
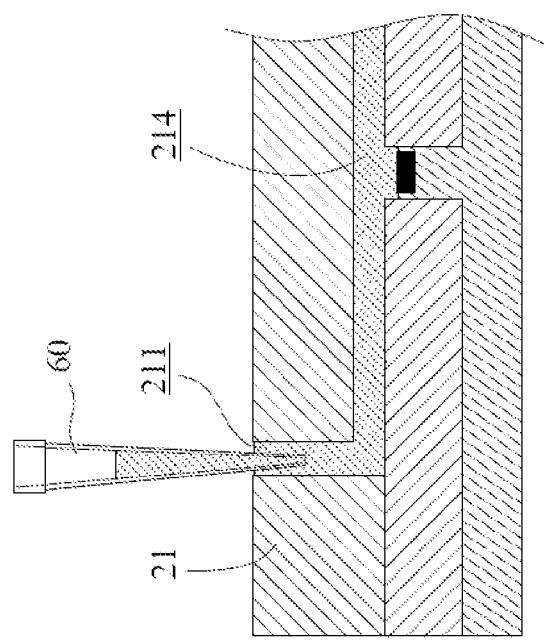
Figure 3D:
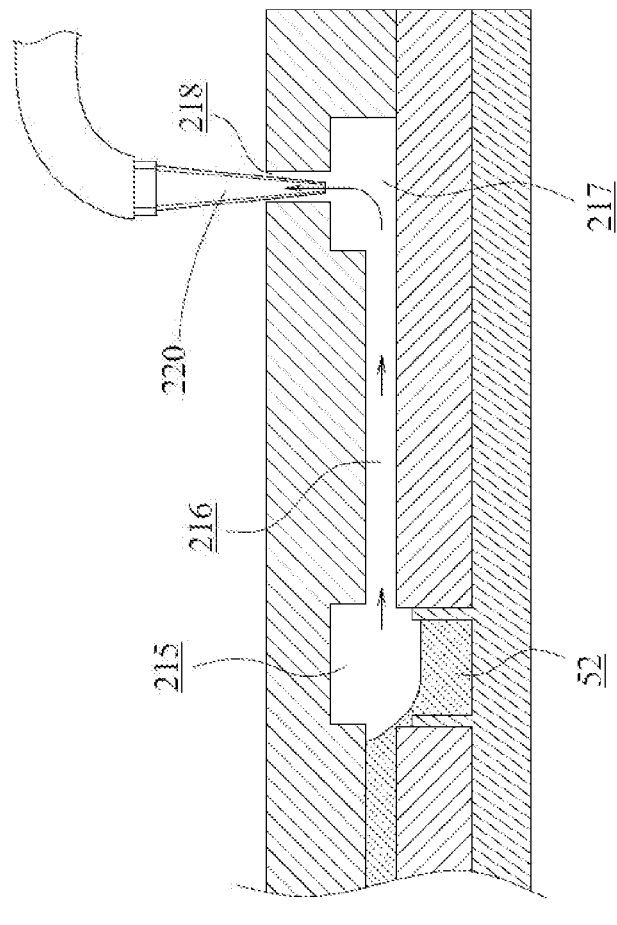
Figure 3D:
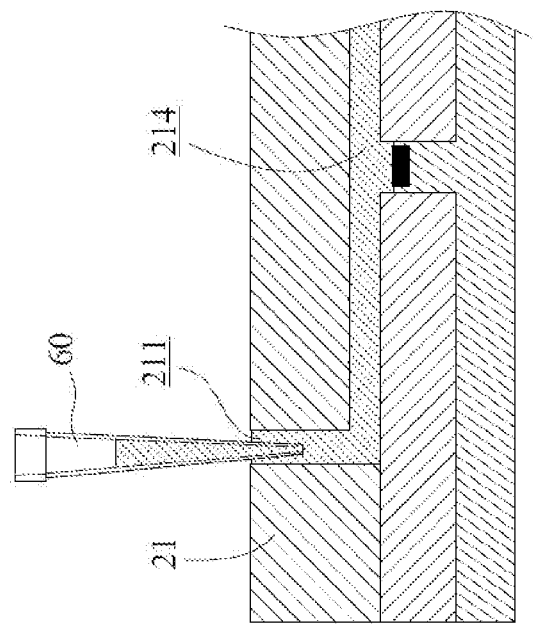

In operation, when applying a "negative pressure" to the air chamber (217) of the microfluidic cell culture chip (10), the liquid in multiple channels can be driven simultaneously from 16 culture medium tanks (212) through the micro-bioreactor (41) to finally reach the waste medium collector tank (52). As shown in FIGS. 3A to 3D, when the microfluidic cell culture chip (10) has completed cells and cell culture medium filling (as shown in FIG. 3A), the pipet (60) is utilized to suck and receive the medium being tested and plugged into the inlet hole (211) directly. Furthermore, a negative pressure tube (220) is connected to the negative pressure source hole (218) (as shown in FIG. 3B) to guide the negative pressure to the sealed chamber in the chip to form negative pressure. A pneumatic tank in the chip is designed to have much lower flow resistance than each pneumatic microchannel, so the pressure in the pneumatic tank will uniformly drop first to cause the pressure drop in each air channel at the same time and guide the culture medium in the front end to flow through 48 micro-bioreactor chambers (41) to reach the waste medium collector tank (52) (as shown in FIG. 3C). With the program to automatically regulate the magnitude of the negative pressure, operation time and pause interval, it is able to adjust the flow rate and estimate the time to fill the waste medium collector tank (52) (as shown in FIG. 3D). Thus, the present invention provides an easy way to not only simultaneously drive culture medium in 48 channels, but also adjust the flow rate.

Figure 4B:
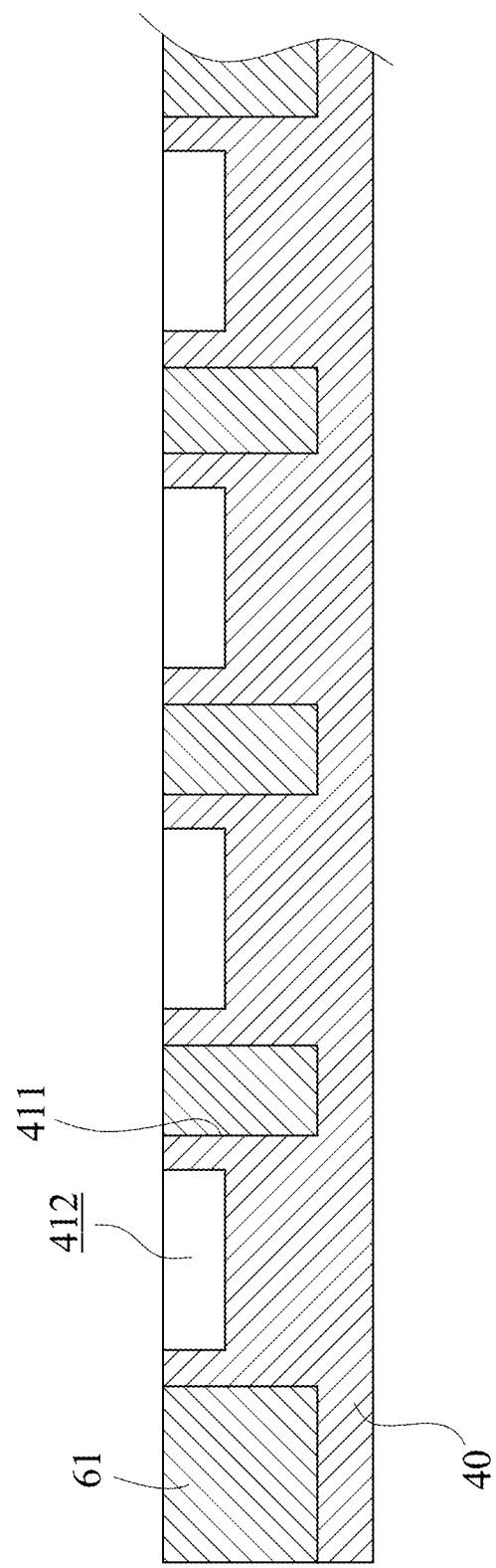
Figure 4C:
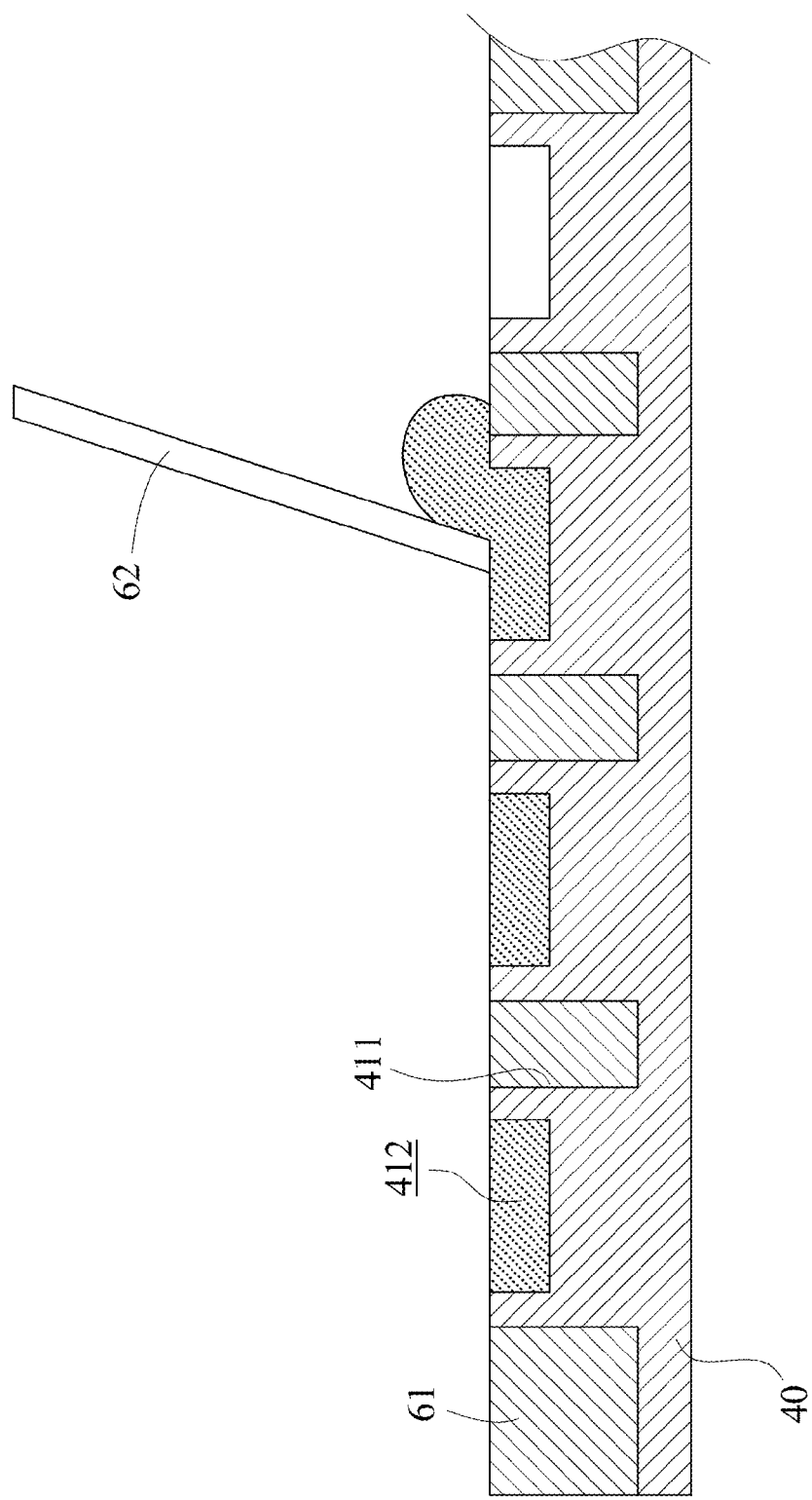
Figure 4D:
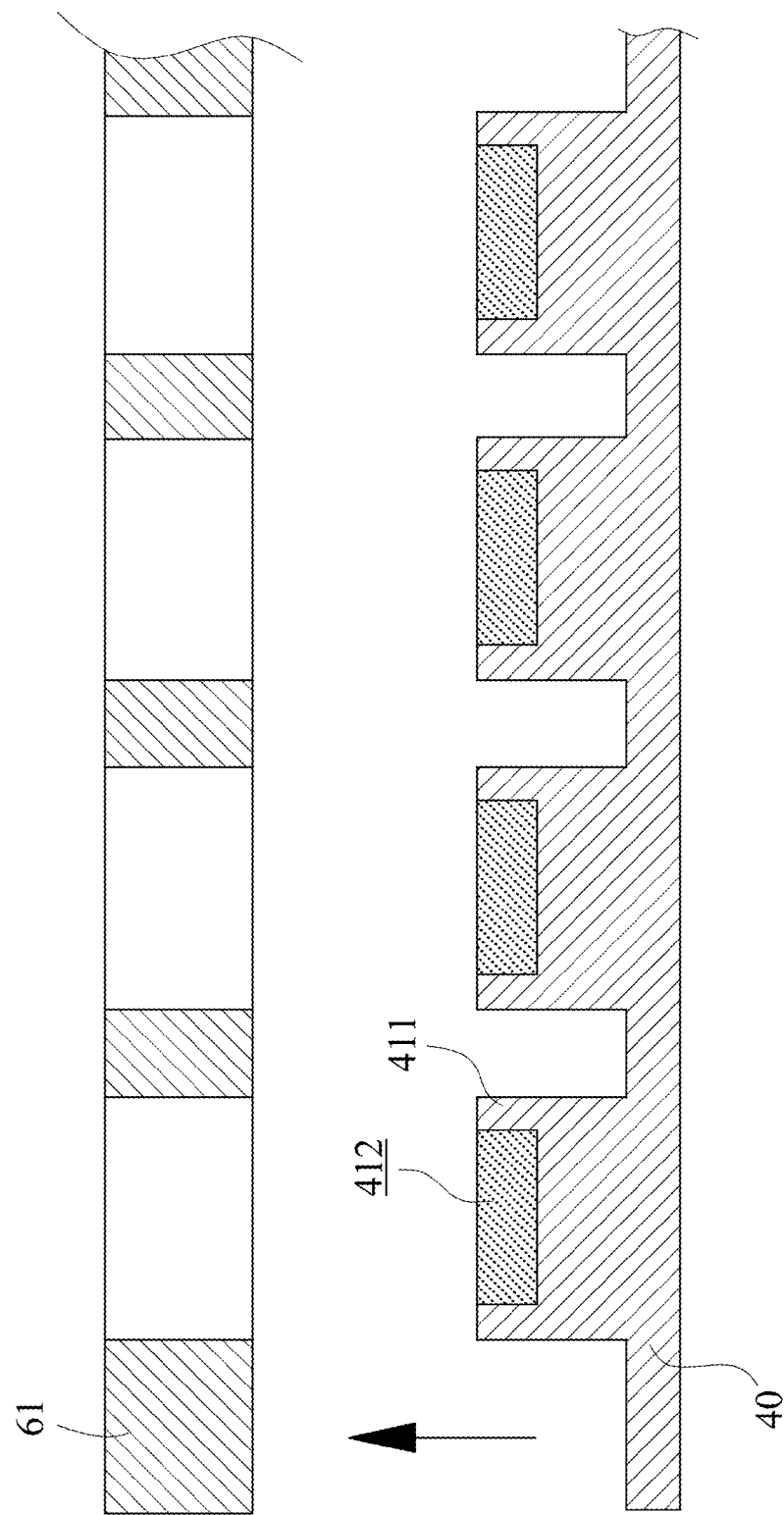

The present invention provides a "microfluidic chip for high throughput miniaturized perfusion-based three-dimensional cell culture" integrating a patent application (application Ser. No. 12/653,335) filed by the same inventor in the present invention, which discloses a method to fill three-dimensional colloidal or biocompatible materials of embedded cells in the bottom plate (40). The operation process is: matching the cylinder (411) of the bottom plate (40) with a colloidal dispersion platform (61) to make it a flat plane, filling three-dimensional colloidal or biocompatible materials of embedded cells into the plane, and using a flat objects (62) (such as a glass plate) to averagely distribute the colloidal suspension in the horizontal direction, so the colloidal suspension can be evenly filled into each cylindrical chamber (412) (micro-bioreactor chamber) of the cylinder (411) (as shown in FIG. 4C) and a plurality of three-dimensional cell culture sample can be prepared quantitatively and quickly in such a manner. Waiting until the colloidal or biocompatible materials to polymerize in the cylinder chambers (412), the bottom plate (40) and the colloidal dispersion platform (61) are separated (as shown in FIG. 4D). Finally, the bottom plate (40) having a plurality of 3-dimensional cell culture samples is directly inserted into the connecting hole (31) of the intermediate plate (30) to achieve a tight engagement to complete the chip configuration.

Figure 5:
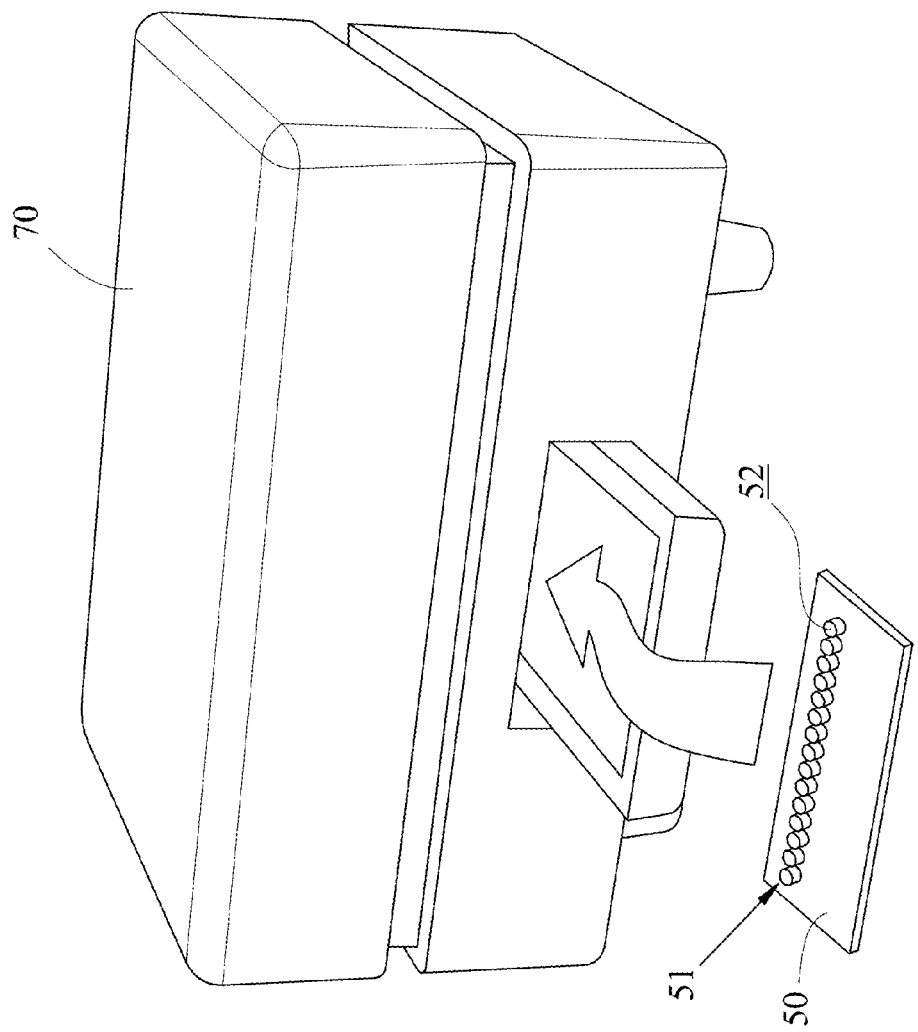
FIG. 5 shows the second bottom plate inserted into the porous microplate analysis equipment.

FIG. 5 illustrates the design of the medium collection analysis area including a plurality of arrays of cylindrical recessed slots (51), which are designed corresponding to the specification of commercial multi-well microplates. The purpose is to connect with the commercial high-throughput biochemical analysis equipment—microplate reader (70) or other compatible biochemical analysis equipment to facilitate the follow-up results of cell culture analysis. In operation, when the cell culture task is completed, the waste medium collector array module (50) can be unloaded, and appropriate analytical reagent can be added to directly analyze the results by using the microplate reader (70) to obtain experimental results from each cell culture medium tank. The present invention can be combined with existing high-throughput analysis equipment that makes the microfluidic cell culture chip (10) have more practical applications.

Figure 6:
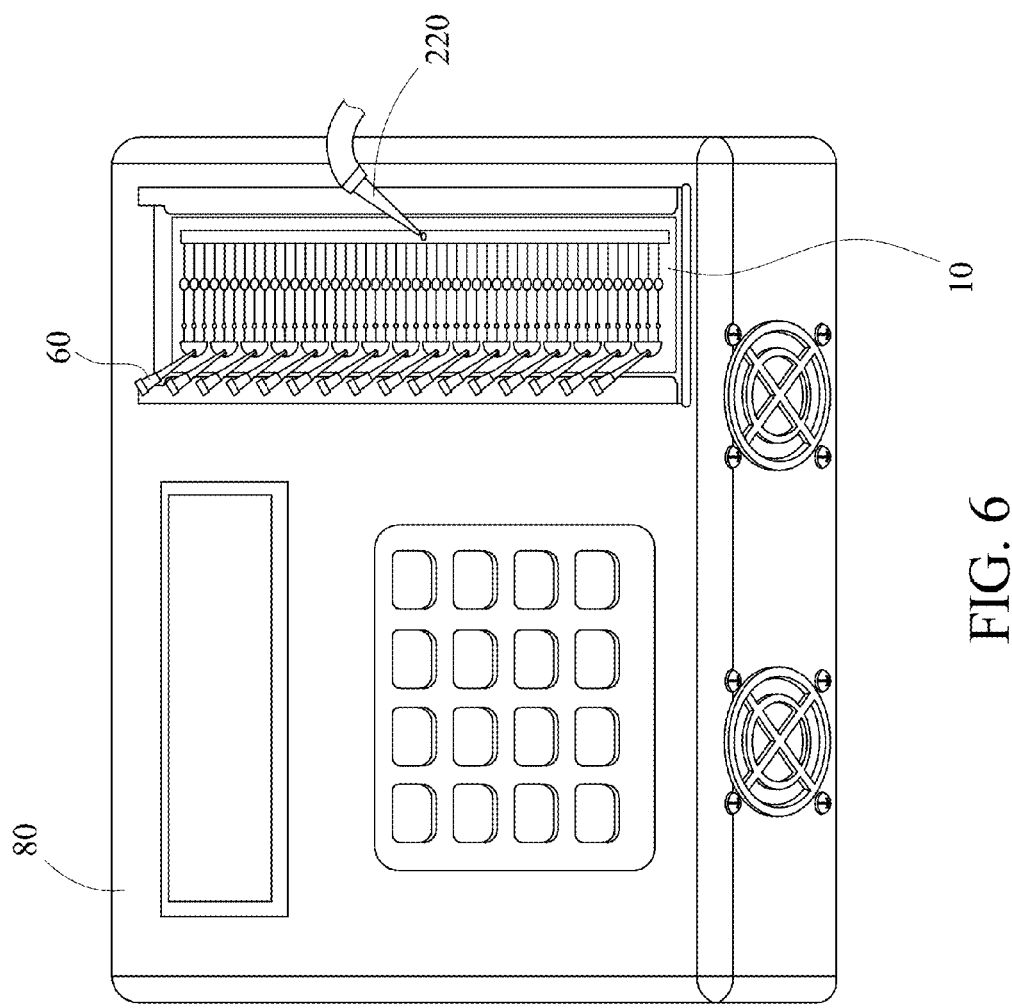
FIG. 6 illustrates the microfluidic chip in the present invention with the control device.

Referring to FIG. 6, a control device (80) is utilized when the cell culture takes place in the present invention, wherein the control device (80) can provide temperature control (at 37° C.) (transparent indium tin oxide glass-based heater associated with a thermal feedback control mechanism) during cell culture, programmable control of the negative pressure, and operation time/pause interval control to regulate the flow rate of cell medium transportation.

Referring to the embodiment shown in FIGS. 2, 6, 7A and 7B, the present invention can be used to investigate the effect of medium pH on the physiology of articular cartilage cells (to verify the functionality and feasibility of the chip). First, preparing the three-dimensional colloidal with embedded chondrocytes (cell density: $2*10^7$ cells $ml^{-1}$, gel type and concentration: agarose, 2%). As illustrated in FIG. 4, filling the three-dimensional colloidal with embedded chondrocytes in the bottom plate (40) of the microfluidic cell culture chip (10). Furthermore, inserting the bottom plate (40) of the microfluidic cell culture chip (10) and waste medium collector array module (50) into the connecting holes (31) or the array holes (32) of the intermediate plate (30) to achieve strong bonding to complete the chip configuration. Next, injecting four cell culture mediums with different pH values (pH: 6.6, 7.0, 7.2 and 7.3) into the tip of pipet (60) connected to the inlet hole (211) of the microfluidic cell culture chip (10) (the culture medium of each pH value injecting into four inlet holes). Finally, using the control device (80) to control the flow rate and temperature –15 μl/hr (negative pressure source: –10 Kpa, negative pressure supply frequency: 0.05 Hz) at 37° C. for a four-day perfusion-type three-dimensional cell culture.

Figure 7A:
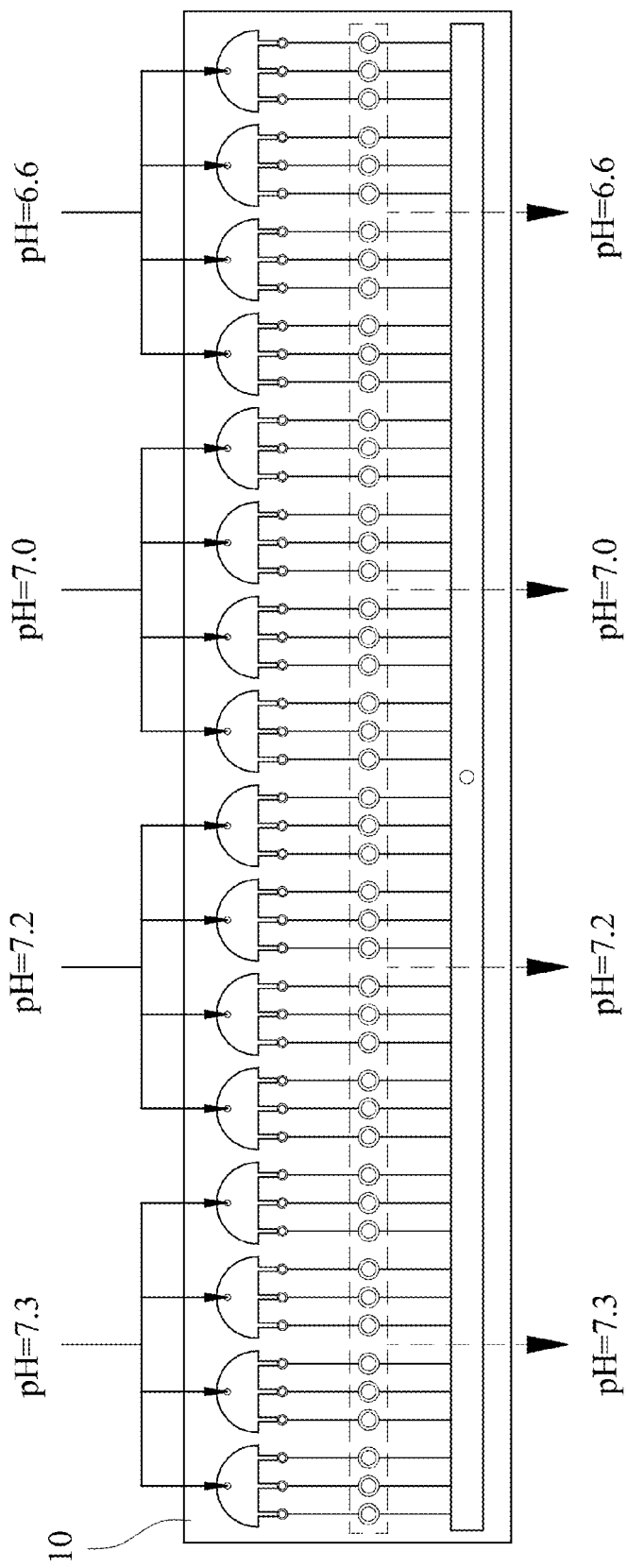
FIGS. 7A and 7B show the experimental results of pH value vs. the effect of lactic acid metabolism of the articular cartilage cells. The experiment is conduct on the microfluidic chip in the present invention.
Figure 7B:
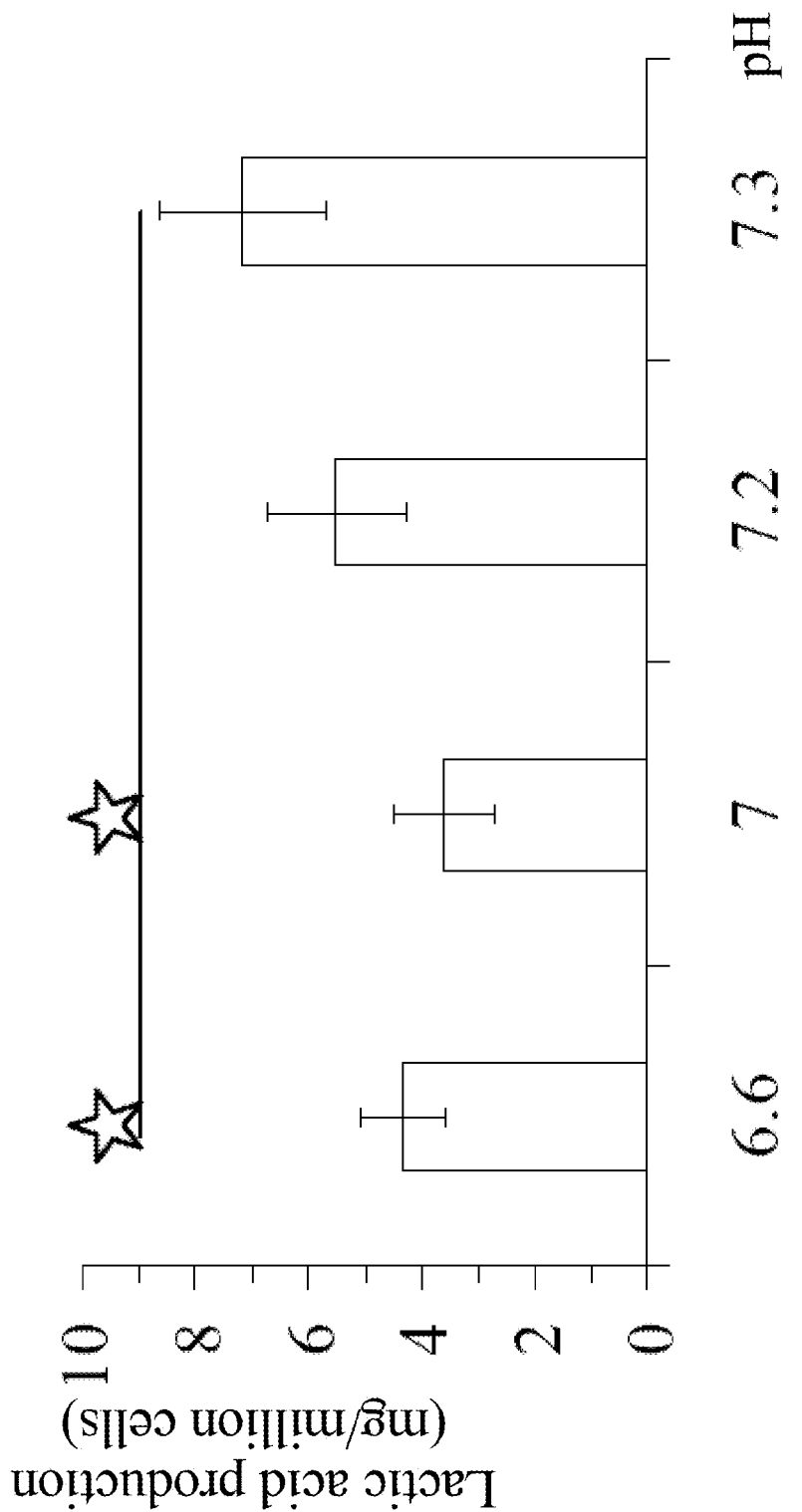
Figure 8:
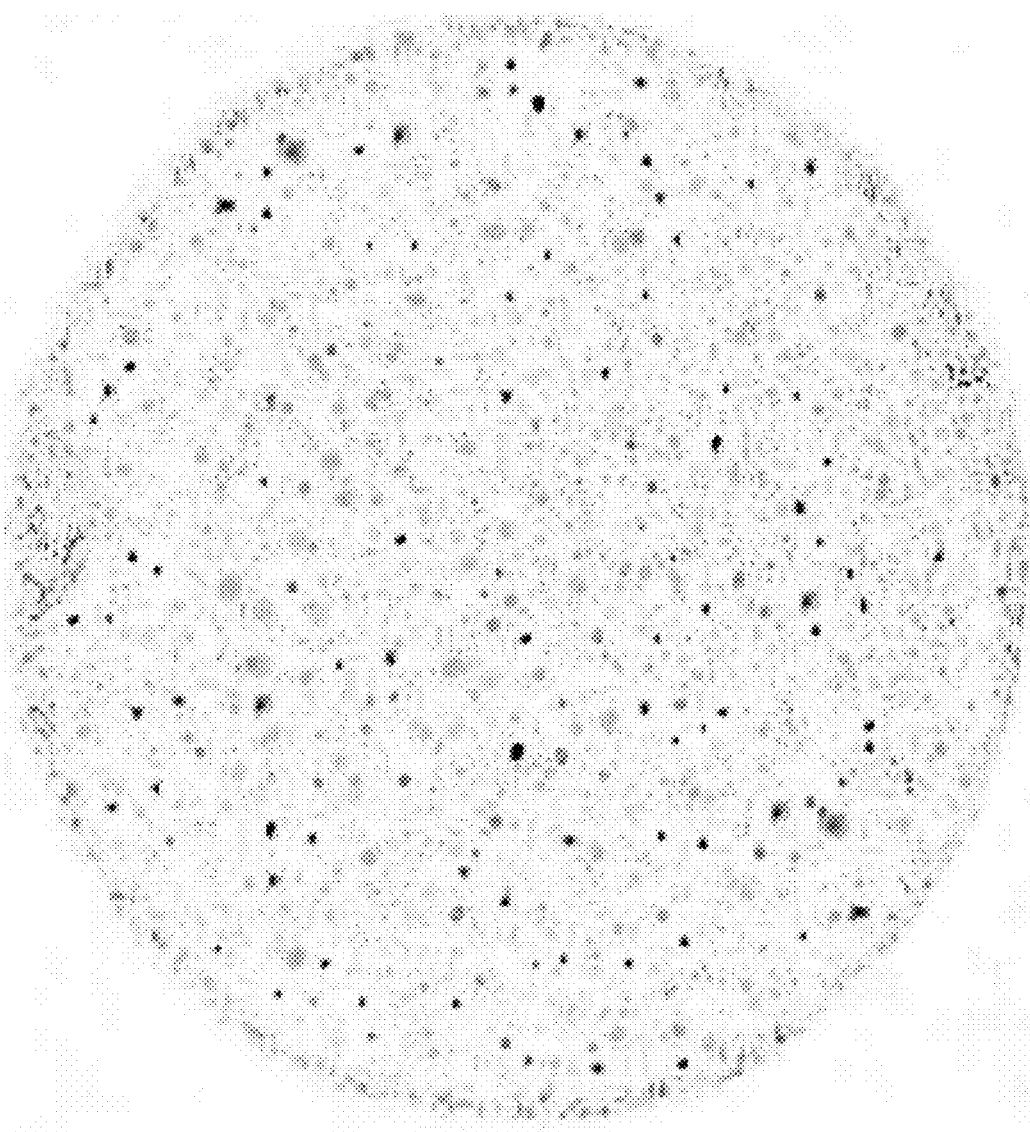
FIG. 8 illustrates the experimental result of pH value vs. the cell viability of the articular cartilage cells (pH=6.6).
Figure 9:
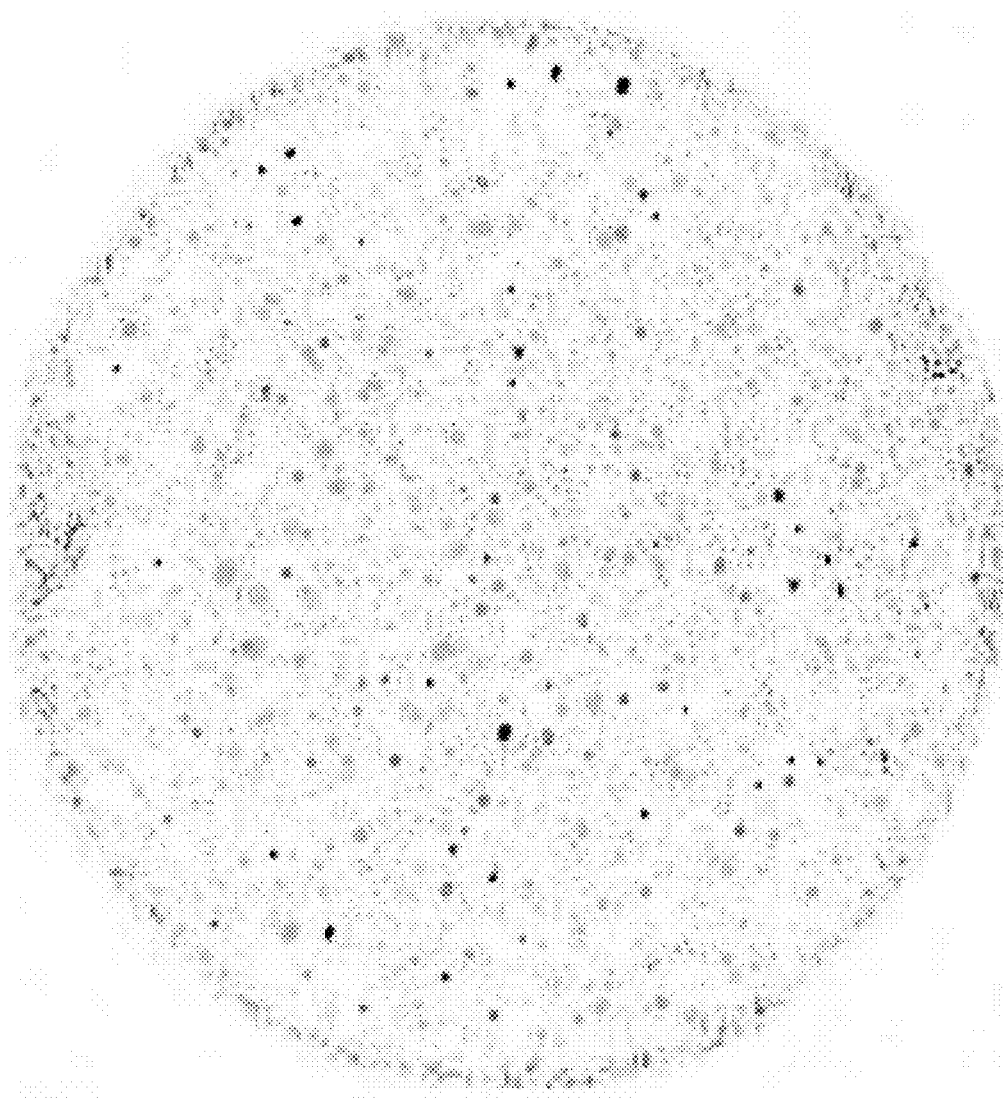
FIG. 9 illustrates the experimental result of pH value vs. the cell viability of the articular cartilage cells (pH=7.0).
Figure 10:
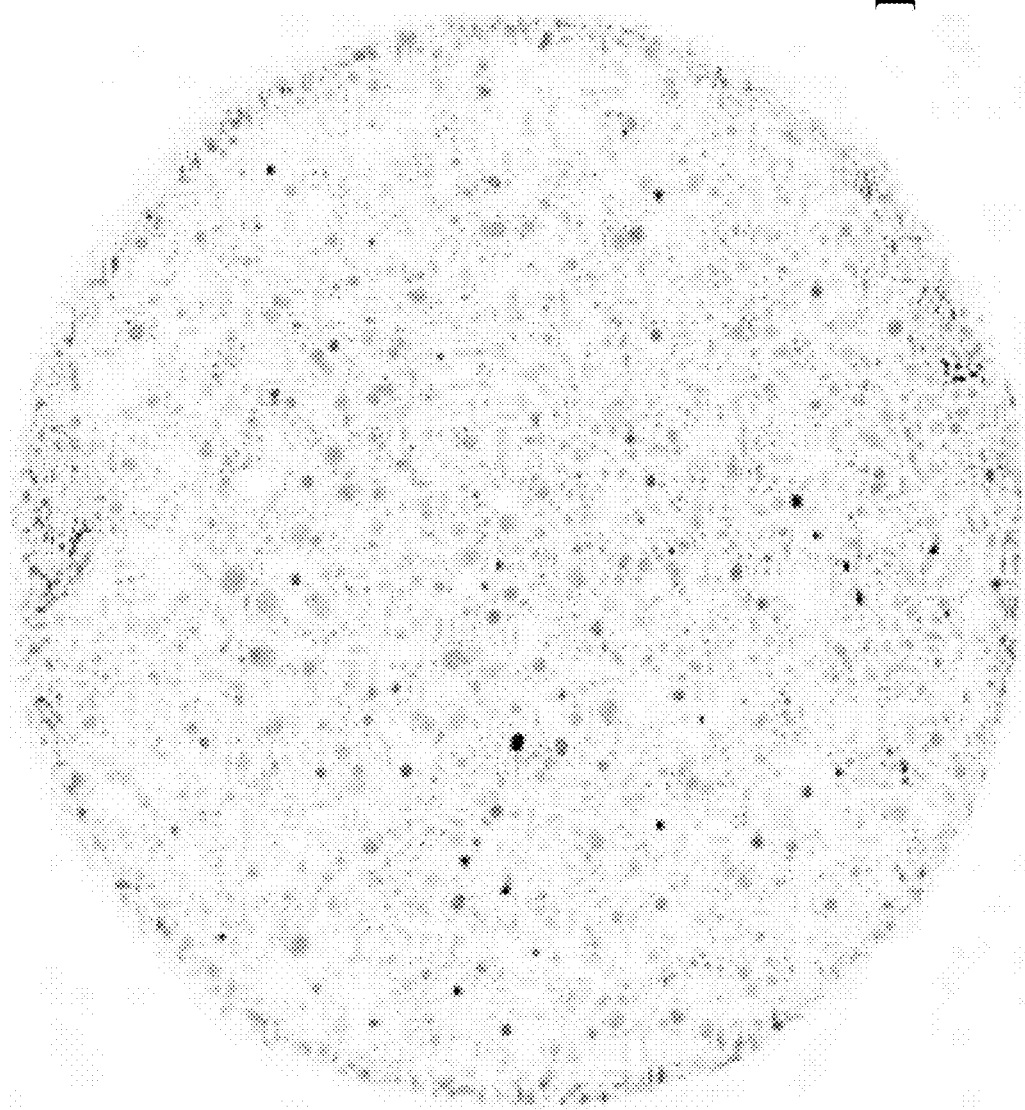
FIG. 10 illustrates the experimental result of pH value vs. the cell viability of the articular cartilage cells (pH=7.2).
Figure 11:
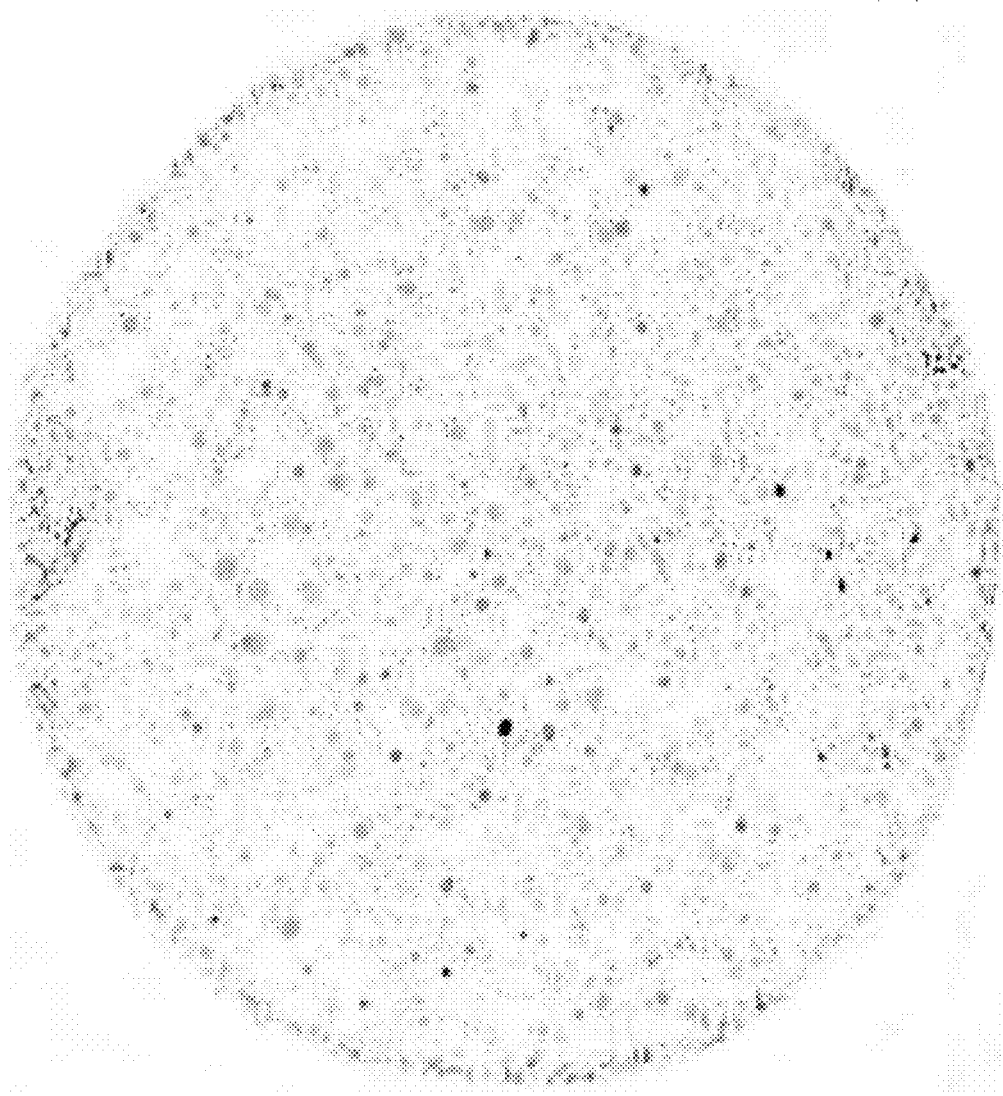
FIG. 11 illustrates the experimental result of pH value vs. the cell viability of the articular cartilage cells (pH=7.3).

After the cell culture is completed, the micro-bioreactor (41) of the bottom plate (40) of the microfluidic cell culture chip (10) is unloaded to determine the viability of chondrocytes by using a fluorescent dye kit and a fluorescent microscopic observation (as shown in FIGS. 8 to 11, the gray point represents a living cell, while the black point represents a dead cell). Experimental results show that the cell viability is as high as 93% under these four conditions, so it is verified that the microfluidic chip for high throughput miniaturized perfusion-based three-dimensional cell culture can be used in cell culture. Furthermore, the waste medium collector array module (50) of the microfluidic cell culture chip (10) can be unloaded and the microplate reader (70) can perform direct analysis of lactic acid collected in the medium in each waste medium collector tank (52). As can be seen in FIG. 5, appropriate amount of lactic acid analysis reagent can be added to each waste medium collector tank (52) of the unloaded waste medium collector array module (50), and the microplate reader (70) can directly analyze the generation of the lactic acid in the medium. As shown in FIGS. 7A and 7B, the results from the microplate reader (70) show that the degree of lactic acid metabolism of the articular cartilage cells varies in the environment of different pH values. Thus, this experiment confirms that the microfluidic chip for high throughput miniaturized perfusion-based three-dimensional cell culture can be successfully combined with existing high-throughput analysis equipment, so that the device of the present invention has more practical applications.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A microfluidic chip for high throughput miniaturized perfusion-based three-dimensional cell culture, including:
   a roof, which has an array of cell culture units at a bottom surface; each cell culture unit including a cell culture medium inlet hole through a top surface of the roof; the bottom surface of the roof having
   a culture medium tank;
   at least one micro-bioreactor;
   at least one waste medium collection and analysis tank;
   a microchannel;
   an air channel;
   an air chamber;
   wherein the culture medium tank is connected with the cell culture medium inlet hole and connected with the at least one micro-bioreactor;
   wherein the at least one micro-bioreactor is coupled to the at least one waste medium collection and analysis tank through the microchannel;
   wherein the at least one waste medium collection and analysis tank is coupled to the at least one micro-bioreactor at a first terminal end, and is coupled to the air chamber at a second terminal end opposite of the first terminal end;
   a negative pressure source hole fluidly connected to the air chamber is coupled to a negative pressure source that generates negative pressure, wherein the negative pressure source drives a medium flow in a single direction from the cell culture medium tank, through the microchannels, and to the waste medium collection and analysis tank;
   an intermediate plate having a plurality of connecting holes and a plurality of array holes;
   a bottom plate detachably coupled to the intermediate plate, wherein the bottom plate has a plurality of cylindrical chambers to matingly insert into the plurality of holes;
   a waste medium collector tray module detachably coupled to the intermediate plate, wherein the module has an array of cylindrical slots to matingly insert into the plurality of array holes.

2. The microfluidic chip for high throughput miniaturized perfusion-based 3-D cell culture of claim 1, wherein the roof, the intermediate plate, the bottom plate and a waste medium collector array module are made by cast molding.

3. The microfluidic chip for high throughput miniaturized perfusion-based 3-D cell culture of claim 1, wherein the roof, the intermediate plate, the bottom plate and a waste medium collector array module are made by injection molding.

4. The microfluidic chip for high throughput miniaturized perfusion-based 3-D cell culture of claim 1, wherein the roof, the intermediate plate, the bottom plate and a waste medium collector array module are made by compression molding.

5. The microfluidic chip for high throughput miniaturized perfusion-based 3-D cell culture of claim 1, wherein the roof, the intermediate plate, the bottom plate and a waste medium collector array module are made by ablation molding.

6. The microfluidic chip for high throughput miniaturized perfusion-based 3-D cell culture of claim 1, further comprising a control device to provide temperature control during cell culture, programmable control of the negative pressure, operation time and pause interval to regulate the flow rate of cell medium transportation.

7. The microfluidic chip for high throughput miniaturized perfusion-based 3-D cell culture of claim 6, wherein the control device provides temperature control at 37° C.

* * * * *